| United States Patent [19] | [11] Patent Number: 4,591,563 |
| --- | --- |
| Paul et al. | [45] Date of Patent: May 27, 1986 |

[54] PROCESS FOR THE PURIFICATION OF DEXTRAN-SUCRASE

[75] Inventors: François Paul, Saint-Orens; Pierre Monsan, Blagnac; Daniel Auriol, Maury, all of France

[73] Assignee: Societe Nationale Elf Aquitaine, Courbevoie, France

[21] Appl. No.: 606,642

[22] Filed: May 3, 1984

[30] Foreign Application Priority Data

May 6, 1983 [FR] France ................. 83 07650

[51] Int. Cl.[4] ................. C12N 9/10; C12R 1/01
[52] U.S. Cl. ................. 435/193; 435/814; 435/816; 435/822
[58] Field of Search ................. 435/193, 814, 816

[56] References Cited

U.S. PATENT DOCUMENTS 4,144,130  3/1979  Kula et al. ................. 435/183
4,508,825  4/1985  Kim et al. ................. 435/816 X

OTHER PUBLICATIONS

Federation Proceedings Abstracts, vol. 40, No. 6, Abstract 672 (1981).

*Primary Examiner*—Lionel M. Shapiro
*Attorney, Agent, or Firm*—Burgess, Ryan & Wayne

[57] ABSTRACT

The invention is directed to a process for the purification of the dextran-sucrase produced by *Leuconostoc mesenteroides* bacteria.

The process according to the invention consists of adding to the culture medium, that contains the extra-cellular enzyme and dextran, a quantity of a PEG type polyether so that, in the medium appear two non miscible phases, that are thus maintained under stirring in order to obtain a good contact. Thereafter the lower dextran phase is separated from the upper polyether phase in order to provide a dextran-sucrase enriched enzymatic preparation.

The purified enzyme can be used in the synthesis processes of the dextrans possessing specific molecular weights for certain applications.

8 Claims, No Drawings

PROCESS FOR THE PURIFICATION OF DEXTRAN-SUCRASE

BACKGROUND OF THE INVENTION

1. Field of the Invention

The present invention concerns a process for the simultaneous purification and concentration of an enzyme, consisting in dextran-sucrase, from the supernatant phase of the culture of the enzyme-producing bacteria.

The dextrans are glucose polymers that are obtained by enzymatic transformation of sucrose. These polysaccharides have various industrial applications depending on their molecular weight. There can be cited as examples the utilization of high molecular weight dextrans in the petroleum industry as viscosigenous agent, the utilization of dextrans of average molecular weight in the foodstuffs industry and that of low molecular weight dextrans in the pharmaceutical industry.

Numerous bacterial layers forming part of the Lactobacillus, Streptococcus or Leuconostoc species possess a dextran-sucrase activity. Among these, however, the strain of Leuconostoc mesenteroides NRRL B 512 (F), that excretes the dextran-sucrase enzyme, when it is cultivated in the presence of sucrose, presents particularly interesting stability properties, an important productivity and a non-pathogenic character, that have allowed it to be utilized on an industrial scale. Furthermore, the dextran-sucrase obtained from this bacterial strain produces an only slightly branched linear dextran (95% α1→6 glycosidic bonds) which is soluble in water, qualities which render it a very worthwhile product on the industrial scale.

Current industrial processes of enzymatic synthesis of dextrans in which the dextran-sucrase of Leuconostoc mesenteroides B 512 (F) is used present, however, drawbacks.

Indeed, the industrial process consists in producing the dextran-sucrase enzyme in very large size fermentation tanks. Once the enzyme has been excreted by the bacteria, L. mesenteroides NRRL B 512 (F), slightly or not purified, it is contacted with its substrate, sucrose, and there is thus produced crude dextran of which the conditions of synthesis cannot be efficiently controlled. This dextran is thereafter subjected to various physicochemical treatments for its recovery and purification; the overall yield of the reaction is thus relatively low.

The present invention concerns an economical purification process of the dextran-sucrase enzyme of Leuconostoc-mesenteroides, able, furthermore, to be easily integrated in an on line production process of the enzyme. The high productivity thus obtained associated with a simple and remarkably efficient purification technique, which is the object of the present invention, justifies the utilization of this enzymatic preparation on the industrial scale and allows, furthermore, through a precise control of the synthesis conditions, the obtention of various types of dextrans according to the field of application envisaged.

Recent developments of enzymatic synthesis have led researchers to take on interest in the problems of purification of enzymes. Numerous purification techniques are utilized with this aim, and by way of example can be cited filtration and its micro- and ultra-filtration embodiments, centrifugation, chromatography, precipitation, liquid-liquid extraction, which has recently been the object of developments involving the phenomenon known as "phase demixing". In this respect there can be cited the works of M. R. KULA (Applied Biochemistry and Bioengineering Vol. 2 pp 71-95 Academic Press 1977 and U.S. Pat. No. 4,144,130) that describe a technique for the purification of various enzymes operating in the phase demixing between two polymers, the polyethylenglycol and the dextran that, at certain concentrations in aqueous solution, become incompatible, thus provoking the appearance of two distinct liquid phases between which are divided the substances present in the medium in function of their solubility of their affinity for one or other of the two phases in the operating conditions.

The culture medium of the strain producing the dextran sucrase contains other extra cellular enzymes that it is important to be able to eliminate. In particular, two saccharolytic enzymes able to utilize the sucrose are excreted by Leuconostoc measenteroides type strains levan-sucrase and invertase. These two enzymes are particularly harmful; on the one hand they reduce the dextran yield, on the other hand, they prevent the satisfactory control of the dextran production. These two contaminating activities can be schematized as follows:

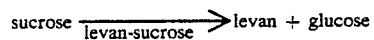

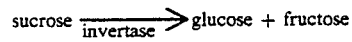

The presence of glucose reveals a contaminating activity; indeed, a pure solution of dextran-sucrase in the presence of sucrose does not produce glucose in the free form. The analysis of the relative percentage of glucose and fructose appearing during purification upon measurement of the dextran-sucrase activity is thus a criterion of the purity of the enzyme.

The object of the present invention is to overcome the previous drawbacks by providing an efficient, simple and economic process of simultaneous purification and concentration of dextran-sucrase operating in an original manner the liquid-liquid extraction by phase demixing.

The present invention concerns a process for the simultaneous purification and concentration of the dextran-sucrase enzyme from the culture medium on sucrose of the Leuconostoc mesenteroides bacteria producing the extra cellular enzyme, the said medium containing dextran, in which, during a first step, an aqueous solution of a polyether is added to the medium in such a quantity such that in the medium, two non-miscible phases appear and said medium is maintained under stirring in order to ensure close and prolonged contact between the two polymers and the biochemical substances; then, in a second step, the lower dextran-rich phase of the medium is separated from the upper polyether-rich phase, the lower phase constituting the dextran-sucrase enriched enzymatic preparation.

The process is expressed by a separation in two phases of the culture medium:
   a heavy dextran-rich phase that contains the concentrated and purified dextran-sucrase enzyme with a partition coefficient $$K = \frac{C \text{ upper phase}}{C \text{ lower phase}}$$

close to zero;

a lighter polyether-rich phase that contains impurities, especially proteins and sugars as well as the contaminating enzymatic activities, phase that is eliminated. By way of usable polyethers in the process according to the invention can be cited:

polyethylenglycol (PEG),
polypropylenglycol, and their derivates such as:

methoxypolyethylenglycol
polyethylenglycol trimethylamine,
polyethylenglycol sulfonate etc. . . .

The average molecular weight of the polyether utilized will generally be between 400 and 20,000. This molecular weight will be chosen in function of the nature of the dextran present in the medium.

The quantity of polyether added will generally be such that the amount in the medium of polyalcohol after addition thereof will be between about 1 and 15% by weight. The optimal amount will be determined in function of the dextran content in the medium.

The process is operated substantially at ambient temperature, i.e. at a maximum temperature of about 30° C. Furthermore, the pH of the medium will generally be between about 4.5 and 7.

It will be advantageous in order to facilitate the carrying out of the process to preferably eliminate, from the medium the cells, for example, by centrifugation.

From the works of M. R. KULA mentioned hereinabove was shown that it was possible to purify enzymes by making use of the phase partition phenomenon. However, it appeared evident that during the purification process the enzymes are distributed between the two phases but that the purified enzyme fraction is obtained solely from the upper PEG phase, the lower dextran phase acting essentially to collect the cellular debris and impurities present in the medium.

Now, it has been observed by the applicant that in the process according to the invention, the quasi totality of the dextran-sucrase enzyme is carried along in the lower dextran phase whereas the other contaminating enzymatic activities preferably pass into the upper polyether phase. The lower dextran phase can also act as a source of dextran-sucrase enzymatic preparations and that as purification is accompanied by a very high concentration, the volume of the lower phase corresponding to. several % of the volume of the medium subjected to the phase partition.

Of course, the process can be carried out in two or several steps during which the lower phase issued from the preceding step will be subjected to a further extraction by phase partition under analogous operating conditions, after having, where necessary, slightly diluted it in order to facilitate the process.

This purification process on several steps can be realized in line in a liquid-liquid extraction column operating at counter-current.

The process of the invention is illustrated by the examples given herein-below, which are to be interpreted at the light of the following definitions.

DEFINITION OF ENZYMATIC ACTIVITIES

Starting from sucrose, three principal enzymatic reactions can be produced:

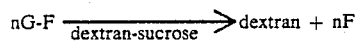

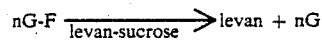

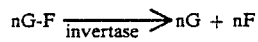

G-F: saccharose
G: glucose
F: fructose

The dextran-sucrase releases exclusively fructose. The levan-sucrase releases exclusively glucose. The invertase releases an equal quantity of fructose and glucose.

If a glucose production is observed during measurement of the saccharolytic activity, it results from a contaminating activity, invertase or levan-sucrase. However, with the aim of allowing the results to be clearly expressed, the production of glucose has been attributed to a levan-sucrase activity that is largely preponderant. Therefore, the levan-scurase activity and the dextran-sucrase activity that appear in the tables are determined as follows:

levan-sucrase activity (ULS): total glucose released
dextran-sucrase activity (UDS): total fructose released
total saccharolytic activity: fructose+glucose.

MEASURING METHODS

1. Measurement of enzymatic activity

In order to specifically proportion the glucose and the fructose, a method of enzymatic titration (hexokinase/ATP, glucose-6-phosphate dishydrogenase/-NADP+, phosphogluco-isomerase) has been utilized.

The total saccharolytic activity is measured by titration of the total reducing sugars (glucose+fructose) by means of the reactive to DNS (dinitro-salicyclic acid); Summer, J. B. *J. Biol. Chem.* 1921 47,5).

2. Measurement of proteins

LOWRY'S method has been utilized {LOWRY, O. H., ROSEBROUGH NM, FARR A. L., and RANDALL, R. M. *J. Biol. Chem.* 193 (1951) 265–275}.

3. Measurement of polymers (dextran or levan)

The polyethylenglycol and oligosaccharides present are first of all eliminated by ultrafiltration in a cartridge of hollow fibers (Amicon) the cut-out threshold of which is 100.000, the polymer is thereafter titrated by using an anthron reactive agent; SCOTT, T. A. and MELVIN, E. H. (1953) *Anal. Chem.* 25, 1656.

The levan is specifically titrated according to the technique described by P. PERLOT, Thesis Doct. Eng. Institut National des Sciences Appliquées, TOULOUSE (1980). It was checked that the dextran did not interfere with this technique.

PRINCIPLE FOR CALCULATING THE ACTIVITY 1 mg of sucrose (molecular weight 342) releases 0.474 mg in the form of polymer (levan or dextran: molecular weight of the monomeric link: 162) and 0.526 mg of free sugar (fructose or glucose: molecular weight 180).

The activity is measured in units per ml of solution or per mg of proteins. One unit represents the conversion of 1 mg of sucrose per hour at 30° C. in the sodium acetate buffer 20mM at pH 5.2.

PRODUCTION OF THE SUPERNATANT PHASE OF THE CULTURE

In a fermentation vat, the Leuconostoc mesenteroides NRRL B 512 (F) bacteria are made to grow in the presence of sucrose. During fermentation, the saccharolytic enzymes and especially dextran-sucrase are excreted in the medium by the bacteria. The dextran-saccharase enzyme synthesizes the dextran in the medium. The fermentation is thus interrupted, the cells present are eliminated by centrifugation and the supernatant phase of the culture is collected in order to be subjected to the purification process.

EXAMPLE 1

In this example, a supernatant phase of a culture obtained as indicated herein-above is treated having a volume of 500 ml by adding progressively thereto 175 ml of an aqueous solution of PEG 1500 at 50% (weight/volume), the homogenization of the medium being ensured by a magnetic stirring.

Thereafter, the lower dextran layer is separated from the upper PEG phase. The fractions of these phases are sampled for analysis. Then, 2.7 ml of the dextran phase is drawn off and diluted to 45 ml by a sodium acetate buffer solution 20mM pH 5.2 and a second separation is carried out by phase partition by adding thereto 11.7 ml of the PEG solution.

The results obtained have been compiled in the following tables.

These results (IA and IB) were obtained after the first step of the process. They display the presence of levans in a substantial quantity (35%) in the culture broth of fermentation which indicates the presence of levan-saccharase. Furthermore, this levan preferentially passes into the PEG phase (90%), unlike the dextran. The results obtained and summarized in table IB show that the simple glucose and fructose sugars preferentially pass into the PEG phase.

The partition coefficients $$K = \frac{\text{(sugar concentration in the } PEG \text{ phase)}}{\text{(sugar concentration in the Dextran phase)}}$$

are respectively 0.84 for the glucose and 0.65 for the fructose (cf. table IC herein-below).

A concentration effect will be observed from examining the results of tables IC since the quasi-totality of the dextran-sucrase activity (90%) is recovered in a volume corresponding to about 5% of the volume of the original solution.

Furthermore, it is observed that the phase partition realized from the supernatant of the culture has the characteristic of being recovered in the lower phase of only 53% dextran present in the original solution that, however, contains 90% of the dextran-sucrase activity.

The results summarized in table 1D show that during the first phase partition the essential of the dextran-sucrase activity passes in the dextran lower phase while the levan-sucrase is equally distributed between the two phases, the partition coefficients being respectively 0.00253 for the dextran-sucrase and 0.033 for the levan-sucrase. During the second phase partition all the dextran-sucrase activity passes in the dextran phase (partition coefficient ~0).

EXAMPLE 2

This example is intended to illustrate the purification of the dextran-sucrase by phase partition in two steps and this in the presence of an added protein (bovine albumin) in order to study its influence on the purification process. During the first step 4144 mg of bovine albumin is added to 200 ml of a supernatant of culture. The supernatant layer is thereafter treated according to the process in two steps described in example 1. During the first step 52 ml of a PEG 1500 solution at 50% weight/volume is added. During the second step, 6 ml of the dextran phase issuing from the first step is drawn off and it is diluted at 33 ml by means of the buffer solution utilized in example 1, and the phase partition is carried out by addition of 10.3 ml of PEG. The results obtained are summarized in table 2. They show a concentration in the dextran phase of the specific dextran-sucrase activity in spite of the presence of proteins that are eliminated from the dextran phase in large proportions (about 90%).

EXAMPLE 3

In this example, according to the process described in example 1, but only comprising one step, 279 ml of a supernatant of culture treated, to which has been added 170.000 exogen invertase units is, through 89 ml of PEG. The aim of adding invertase units is to study the influence of the presence of excess invertase on the quality of the purification.

The results are summarized in table 3A. It is observed that the presence in excess of invertase units in no way modifies the purification of the dextran-sucrase in the dextran phase, more than 97% of the invertase units passing into the upper PEG phase.

The yields are indicated in table 3B; the partition coefficients obtained are respectively 0.002 for the dextran-sucrase and 1.37 for the invertase.

EXAMPLE 4

In this example, 40 ml of an already purified dextran-sucrase solution is treated in a single purification step, in the presence of exogen invertase by adding to the medium 13.5 ml of the PEG solution.

The results obtained are summarized in table 4. It will be observed, as in previous example 3, that no further dextran-sucrase activity remains in the PEG phase, while the essential of the invertase activity subsists in the upper PEG phase.

EXAMPLE 5

In this example, 150 ml of a supernatant of fermentation is treated according to the process of the invention, but subjecting it to five successive phase partition which on the quantitative level is representative of what can be obtained in an extraction column operating unbrokenly. The results obtained are summarized in table 5A. It can be observed that practically all the dextran-sucrase activity has remained in the dextran phase with a concentration factor of more than 20.

Further, more than 75% levan-sucrase units have been eliminated. The specific activity has been multiplied more than a thousand fold. The partition coefficient of the dextran-sucrase is close to 0.002. The yields are illustrated in table 5B.

Finally, it should be observed that the concentration and purification are carried out in a stabilizing environment that is accompanied by a rapid elimination of the residual sucrose issuing from the fermentation and thus allows the interruption of the dextran synthesis in the absence of substrate; it is indeed important to limit to a maximum the dextran concentration in the enzymatic solution.

TABLE 1A

|  | Total polysaccharides | Levan | Levan % |
|---|---|---|---|

|  | Vol (ml) | (g) | (g) | (weight) |
|---|---|---|---|---|
| supernatant of fermentation | 500 | 4.65 | 1.64 | 35 |
| PEG phase | 655 | 1.9 | 1.47 | 75 |
| dextran phase | 20 | 2.45 |  |  |

TABLE 1B

|  | Volume (ml) | glucose (%) | fructose (%) |
|---|---|---|---|
| supernatant of fermentation | 500 | 100 | 100 |
| PEG phase | 655 | 96.5 | 95.5 |
| dextran phase | 20 | 3.5 | 4.5 |

TABLE 1D

|  | DEXTRAN-SUCROSE YIELD |
|---|---|
| FIRST PHASE PARTITION |  |
| supernatant phase of fermentation (solution to purify) | 100 |
| PEG phase (upper) | 7.5 |
| dextran phase (lower) | 90 |
| SECOND PHASE PARTITION |  |
| original solution | 100 |
| PEG phase (upper) | — |
| dextran phase (lower) | 83.5 |

TABLE 1C

|  | volume ml | saccharolytic units | U.D.S. (mg sucrose per hour) | U.L.S. (mg sucrose per hour) | protein mg | specific activity U.D.S./mg protein |
|---|---|---|---|---|---|---|
| 1st phase partition |  |  |  |  |  |  |
| original solution | 500 | 76 500 | 67 420 | 9 090 | 2 809 | 24 |
| PEG phase (upper) | 655 | 9 381 | 5 045 | 4 336 | 2 402 | 2 |
| dextran phase (lower) | 20 | 64 688 | 60 710 | 3 978 | 110 | 555 |
| 2nd phase partition |  |  |  |  |  |  |
| original solution | 45 | 8 844 | 8 188 | 656 | 16.2 | 510 |
| PEG phase (upper) | 54.3 | 97 | 1 | 96 |  |  |
| dextran phase (lower) | 2.4 | 7 294 | 6 816 | 478 | 2.7 | 2 559 |

TABLE 2

|  | volume ml | U.D.S. | U.L.S. | original protein mg | albumin exogen mg | total protein mg | specific activity U.D.S./mg protein |
|---|---|---|---|---|---|---|---|
| 1st phase partition |  |  |  |  |  |  |  |
| original solution | 200 | 26 968 | 3 632 | 1 106 | 4 144 | 5 250 | 5.2 |
| PEG phase (upper) | 244 | ~0 | 952 |  |  | 4 628 | 0 |
| dextran phase (lower) | 18 | 25 513 | 2 732 |  |  | 292 | 87.4 |
| 2nd phase partition |  |  |  |  |  |  |  |
| original solution | 33 | 8 429 | 901 | 96 | 785 | 881 | 9.6 |
| PEG phase (upper) | 40.7 | 37 | 18 |  |  | 674 | 0.1 |
| dextran phase (lower) | 2.6 | 7 268 | 911 |  |  | 222 | 32.7 |

TABLE 3A

|  | volume ml | U.D.S. | Invertase units | Proteins mg | Specific activity U.D.S/mg protein |
|---|---|---|---|---|---|
| original solution | 279 | 30 413 | 169 354 | 2 020 | 15.1 |
| PEG phase (upper) | 354.8 | 0 | 162 000 | 1 983 | ~0 |
| dextran phase (lower) | 13.2 | 28 927 | 4 378 | 173 | 164.3 |

TABLE 3B

| Yield | Dextran Sucrase | Invertase |
|---|---|---|
| original solution | 100 | 100 |
| PEG phase (upper) | — | 96 |

TABLE 3B-continued

| Yield | Dextran Sucrase | Invertase |
|---|---|---|
| Dextran phase (lower) | 95 | 2.6 |

TABLE 4

| | volume ml | U.D.S. | Invertase units | Proteins mg | Specific activity U.D.S/mg protein |
|---|---|---|---|---|---|
| original solution | 40 | 2 203 | 5 330 | 1.6 | 1 377 |
| PEG phase (upper) | 51 | ~0 | 4 873 | — | — |
| dextran phase (lower) | 2.5 | 1 735 | 286 | 0.92 | 1 886 |

TABLE 5A

| | volume ml | U.D.S. units dextran-sucrose | U.L.S. units sucrose | Proteins mg | Specific activity U.D.S/mg protein |
|---|---|---|---|---|---|
| supernatant phase of fermentation (solution to be purified) | 150 | 16 815 | 2 535 | 962 | 18 |
| Dextran phase (lower) after 5 partitions | 7 | 15 885 | 615 | 0.75 | 21 180 |

TABLE 5B

| | U.D.S. | U.D.S. YIELD | U.L.S. | U.L.S. YIELD |
|---|---|---|---|---|
| original solution | 16 815 | 100 | 2 535 | 100 |
| PEG phase | 721 | 4.3 | 1 815 | 71.6 |
| Dextran phase after 5 partitions | 15 885 | 94.5 | 615 | 24.3 |

We claim:

1. A process for the simultaneous purification and concentration of the dextran sucrase enzyme from the culture medium in which *Leuconostoc mesenteroides* bacteria are grown on sucrose to produce the extra cellular enzyme, the said medium containing dextran, which process comprises the steps of:
   (a) adding to said medium an aqueous solution of a polyglycol in an amount such that said dextran and polyglygol form two non-miscible phases;
   (b) maintaining said medium under stirring conditions in order to ensure close and prolonged contact between the two phases, and
   (c) separating a dextran-rich first phase of the medium from the polyether-rich second phase, the first phase constituting a dextran sucrase enriched enzymatic preparation.
2. The process according to claim 1, wherein the polyglycol has a molecular weight between about 400 and 20,000.
3. The process according to claim 1 or 2, wherein the content of the medium in polyglycol after addition is between about 1 and 15% by weight.
4. The process according to claim 1 or 3, wherein it is carried out at a temperature not greater than about 30° C. and a pH between about 4.5 and 7.
5. The process according to claim 1, 2, 3 or 4, wherein the culture medium is previously treated in order to eliminate the cells.
6. The process according to claim 1, 2, 4 or 5 wherein it is carried out in several successive steps, the treated solution at each step being constituted by the dextran phase collected at the issue of the preceding step.
7. The process according to claim 6, wherein it is carried out continuously in a liquid-liquid extraction column operating at counter-current.
8. The process according to claim 1, 2, 3, 4, 5, 6 or 7, wherein it is utilized in the purification of the dextran sucrase enzyme of the *Leuconostoc mesenteroides* NRRL B 512 (F) bacteria.

* * * * *